(12) United States Patent
Jurbala

(10) Patent No.: US 8,771,304 B1
(45) Date of Patent: *Jul. 8, 2014

(54) DEVICE FOR MINIMALLY INVASIVE TENDON SHEATH RELEASE HAVING STATIC BLADE

(71) Applicant: Brian Michael Jurbala, Lakeland, FL (US)

(72) Inventor: Brian Michael Jurbala, Lakeland, FL (US)

(73) Assignee: SonicSurg Innovations, LLC, Lakeland, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/090,714

(22) Filed: Nov. 26, 2013

Related U.S. Application Data

(62) Division of application No. 12/896,088, filed on Oct. 1, 2010, now Pat. No. 8,608,763.

(60) Provisional application No. 61/251,957, filed on Oct. 15, 2009.

(51) Int. Cl.
*A61B 17/32* (2006.01)

(52) U.S. Cl.
USPC ......................................................... 606/170

(58) Field of Classification Search
USPC .......... 128/898; 600/114, 183; 606/166, 167, 606/138, 148, 150, 170, 190, 191, 79; 30/62, 254, 289, 294
See application file for complete search history.

(56) References Cited

U.S. PATENT DOCUMENTS

| | | | | |
|---|---|---|---|---|
| 2,764,814 A | * | 10/1956 | Jecker | 30/294 |
| 3,365,798 A | * | 1/1968 | Cunningham | 30/287 |
| 3,975,822 A | * | 8/1976 | Mabus | 30/294 |
| 4,963,147 A | * | 10/1990 | Agee et al. | 606/170 |
| 5,273,024 A | * | 12/1993 | Menon et al. | 600/114 |
| 5,282,816 A | * | 2/1994 | Miller et al. | 606/167 |
| 5,323,765 A | * | 6/1994 | Brown | 600/104 |
| 5,325,883 A | * | 7/1994 | Orr | 128/898 |
| 5,353,812 A | * | 10/1994 | Chow | 128/898 |
| 5,387,222 A | * | 2/1995 | Strickland | 606/167 |
| 5,423,804 A | * | 6/1995 | Kulick | 606/14 |
| 5,480,408 A | * | 1/1996 | Chow | 606/167 |
| 5,507,800 A | * | 4/1996 | Strickland | 606/167 |
| 5,531,232 A | * | 7/1996 | Hill | 128/898 |
| 5,620,446 A | * | 4/1997 | McNamara et al. | 606/79 |
| 5,782,850 A | * | 7/1998 | Ro | 606/167 |
| 5,957,944 A | * | 9/1999 | Khuri et al. | 606/170 |
| 6,179,852 B1 | * | 1/2001 | Strickland et al. | 606/167 |
| 7,611,521 B2 | * | 11/2009 | Lubbers et al. | 606/104 |
| 2005/0228426 A1 | * | 10/2005 | Campbell | 606/192 |
| 2006/0095059 A1 | * | 5/2006 | Bleich et al. | 606/170 |
| 2006/0190021 A1 | * | 8/2006 | Hausman et al. | 606/167 |

(Continued)

*Primary Examiner* — David Eastwood
(74) *Attorney, Agent, or Firm* — Michele L. Lawson; Smith & Hopen, P.A.

(57) ABSTRACT

A device for minimally invasive tendon sheath release is presented. The device enables a surgeon to cut ("open") a pulley that is obstructing a nodule and keeping a tendon from sliding smoothly. The device is generally comprised of a sheath having a guide probe and a dorsal outrigger guide between which a cutting blade is positioned. The device is inserted through a small incision and the guide probe is used to find the edge of the pulley. Once found, the probe is guided to an end of the pulley. After proper position is assured, a cutting blade is deployed The entire device is then pushed or pulled using the device handle along the pulley until the pulley is completely released or where resistance is no longer felt.

8 Claims, 10 Drawing Sheets

(56) References Cited

U.S. PATENT DOCUMENTS

| | | | |
|---|---|---|---|
| 2007/0112366 A1* | 5/2007 | Welborn et al. | 606/170 |
| 2007/0288043 A1* | 12/2007 | Rehnke | 606/170 |
| 2008/0109021 A1* | 5/2008 | Medoff | 606/167 |
| 2008/0195128 A1* | 8/2008 | Orbay et al. | 606/170 |
| 2008/0200758 A1* | 8/2008 | Orbay et al. | 600/112 |
| 2008/0221579 A1* | 9/2008 | Panchbahavi | 606/79 |
| 2009/0048616 A1* | 2/2009 | Gonzalez-Hernandez | 606/148 |
| 2009/0228022 A1* | 9/2009 | McClellan | 606/139 |
| 2009/0270856 A1* | 10/2009 | Saadat et al. | 606/33 |
| 2010/0069936 A1* | 3/2010 | Palmer et al. | 606/167 |
| 2011/0252651 A1* | 10/2011 | Sewell | 30/289 |

* cited by examiner

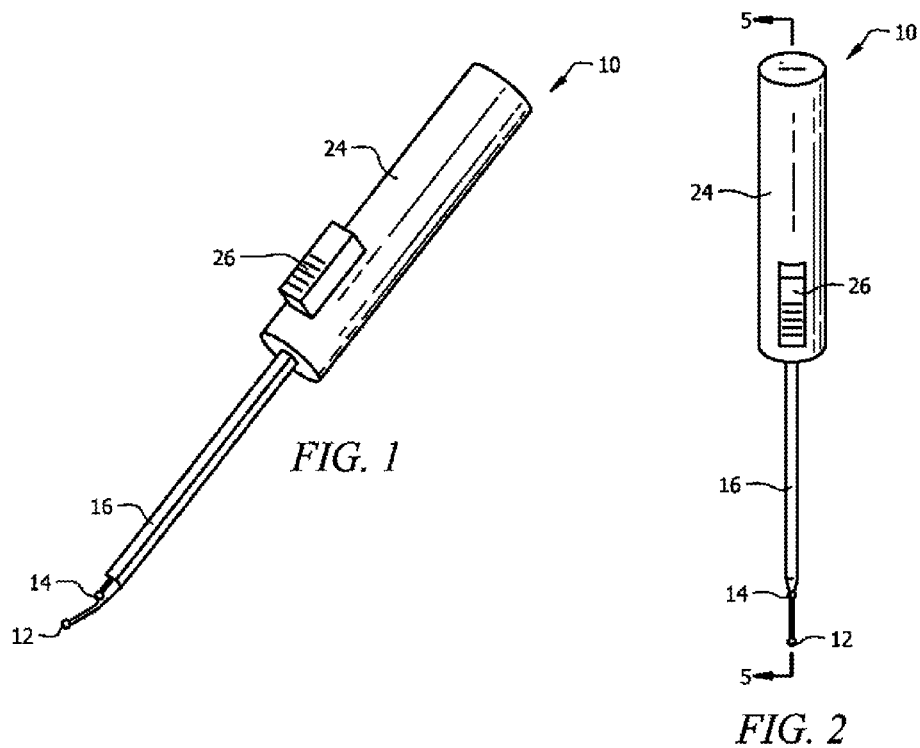
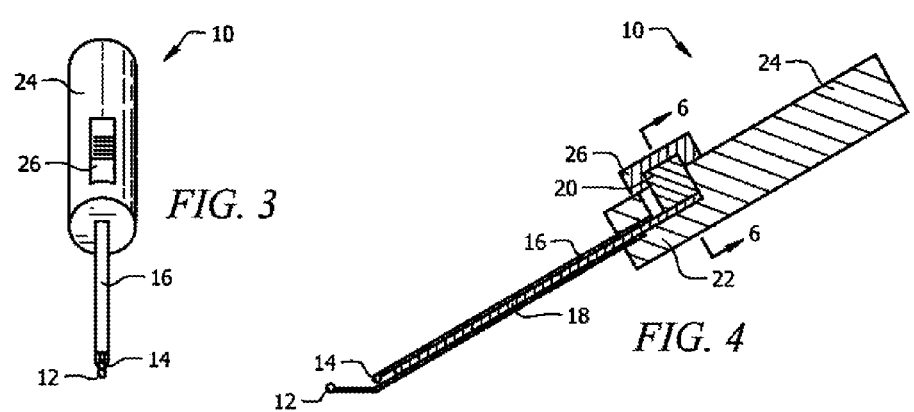

DEVICE FOR MINIMALLY INVASIVE TENDON SHEATH RELEASE HAVING STATIC BLADE

CROSS REFERENCE TO RELATED APPLICATION

This application is a divisional of and claims priority to currently pending U.S. patent application Ser. No. 12/896,088, entitled "Method for Minimally Invasive Tendon Sheath Release", filed on Oct. 1, 2010, which claims priority to U.S. Provisional Patent Application No. 61/251,957, entitled "Device for Minimally Invasive Tendon Sheath Release," filed on Oct. 15, 2009, the contents of each of which are hereby incorporated by reference.

BACKGROUND OF THE INVENTION

1. Field of the Invention

This invention relates to a novel device and method for minimally invasive tendon sheath release. More particularly, it relates to a device and method that allows a surgeon to cut ("open") a pulley that is obstructing a nodule and keeping a tendon from sliding smoothly.

2. Description of the Prior Art

Tendons that move fingers are held in place on bones by a series of ligaments called pulleys (or sheath). These ligaments form an arch on a bone surface that creates a sort of tunnel through which the tendon extends along the extent of the bone. Triggering is usually the result of a thickening in the tendon that forms a nodule, or knob. The pulley ligament may thicken as well. The constant irritation from the tendon repeatedly sliding through the pulley causes the tendon to swell in this area and create the nodule.

The symptoms of trigger finger include pain and a funny clicking sensation when the finger is bent. Pain usually occurs when the finger is bent and straightened. Tenderness usually occurs over the area of the nodule. The clicking sensation occurs when the nodule moves through the tunnel formed by the pulley ligaments. With the finger straight, the nodule is at the far edge of the surrounding ligament. When the finger is flexed, the nodule passes under the ligament and causes the clicking sensation. If the nodule becomes too large it may pass under the ligament and become stuck at the near edge. The nodule cannot move back through the tunnel causing the finger to lock in the flexed trigger position. Surgery may be required to release the trigger finger.

Trigger finger and tendon sheath surgery are common procedures that are usually performed in the operating room. Traditional tendon sheath release procedure is performed in an operating room at a hospital or surgery center under conscious sedation—which involves risk to the patient—and using a local anesthetic. The traditional open operation uses a conventional scalpel device and a 1.5 to 2.0 cm incision that disrupts all tissue and skin above the pulley and requires two or three stitches.

What is needed is a device and method that allows the operation to be performed in a surgeon's office safely, quickly, and in a less costly manner than going to the operating room. However, in view of the prior art considered as a whole at the time the present invention was made, it was not obvious to those of ordinary skill in the art how the limitations of the art could be overcome.

SUMMARY OF INVENTION

The long-standing but heretofore unfulfilled need for an improved device and method for minimally invasive tendon sheath release that allows the operation to be performed in a surgeon's office safely, quickly, and in a less costly manner than going to the operating room is now met by a new, useful, and nonobvious invention.

Generally speaking, the claimed invention is a precisely guided scalpel device that allows a surgeon to perform a tendon sheath release procedure safely and quickly in an office. The procedure is performed through an incision about 90 to 95% smaller than a conventional incision while at the same time allowing for minimal dissection of surrounding tissue and a more precise release of the pulley. Probes at the tip of the device allow the user to ensure that the device is appropriately positioned under the pulley and, when this is confirmed under fluoroscopy or ultrasound, the retractable knife portion of the device can be deployed and the pulley safely cut and divided, thereby disturbing much less surrounding tissue than a conventional operation.

In a first embodiment, the device includes a handle, a handle cavity, a sliding flag and switch, a sheath extending from the cavity and handle, a retractable shaft within the sheath, a spherical tipped guide probe, and a dorsal outrigger tipped guide. The spherical tipped guide probe attaches to the distal bottom tip of the sheath. The dorsal outrigger spherical tipped guide is attached to the distal top of the sheath. The sheath contains the retractable cutting shaft and is attached to the handle. The handle contains a tunnel that is essentially an extension of the sheath within the handle and extends to the handle cavity. The sliding flag and switch are attached to the retractable cutting blade. The handle slot contains and guides the proximal part of the retractable cutting shaft and its attached sliding flag. The sliding flag links the retractable cutting shaft to the blade deployment switch. The sliding flag and deployment switch essentially form a trigger mechanism for deploying the blade.

The dorsal outrigger guide and guide probe have tips that are spherical shaped. However, the tips may be any shape.

In an embodiment, the dorsal outrigger guide extends and retracts with the retractable cutting shaft.

In an embodiment, the dorsal outrigger guide is angled relative to the sheath, and the guide probe is tapered or curved.

In an embodiment, the retractable cutting shaft may include a crochet hook type blade tip. The sheath may also be curved.

In an embodiment, the blade is in mechanical communication with the deployment switch via a wire.

In alternate embodiment, the cutting shaft is not slidable; instead, the cutting shaft is affixed at the distal end of the sheath between the dorsal outrigger guide and the guide probe. In this embodiment, the trigger mechanism is unnecessary.

In an additional alternate embodiment, the shaft is turned up at the tip for placement under the pulley. A sliding blade slides along the shaft dividing the pulley by pushing the sliding blade itself rather than the whole instrument.

The method of performing the procedure includes the following steps. First, the involved finger is identified, verified, prepped, and draped in a sterile fashion. Next, 2 to 3 cc of local anesthetic is injected at the level of the A-1 pulley. A 3 to 4 mm incision is made at, or just proximal to, the proximal flexion crease of the finger. A small pair of tenotomy scissors are used to dissect in the subcutaneous tissue above the tendon sheath proximally to the interval between the A-1 and A-2 pulley in the midline of the finger. The spherical tipped guide is inserted into the interval between the A-1 and A-2 pulleys and directed distal to proximal between the A-1 pulley dorsally and the flexor tendons and directed proximally in the direction of the flexor tendon sheath (i.e., toward the valley between the thenar and hypothenar eminences at the carpal tunnel). Once the dorsal outrigger guide engages/passes under the proximal edge of the A-1 pulley, the instrument is wiggled in the plane of the palm to confirm central placement underneath the A-1 pulley. Additional confirmation of the instrument within the tendon sheath may be confirmed by ultrasonic or fluoroscopic imaging. The novel device is then pushed distal to proximal in the direction of the thenar/hyppothenar valley. Resistance is felt as the blade engages and begins to divide the pulley. The instrument is slowly pushed approximately 1 to 1.4 cm at which time a noticeable decrease in resistance is felt signaling the complete division of the pulley. At this point, the instrument is backed out and removed from the wound and the patient is asked to flex and extend the finger to confirm complete division of the pulley. The incision is either closed with a single stitch, a steri-strip, or derma bond glue. A sterile band aid is then placed over the wound. The patient can begin immediate range of motion exercises.

BRIEF DESCRIPTION OF THE DRAWINGS

For a fuller understanding of the invention, reference should be made to the following detailed description, taken in connection with the accompanying drawings, in which:

FIG. 1 is a perspective view of an embodiment of the device utilizing a blade deployment mechanism;

FIG. 2 is a top view of an embodiment of the device utilizing a blade deployment mechanism;

FIG. 3 is a front view of an embodiment of the device utilizing a blade deployment mechanism;

FIG. 4 is a cross sectional side view of an embodiment of the device utilizing a blade deployment mechanism;

DETAILED DESCRIPTION OF THE PREFERRED EMBODIMENT

The following detailed description discloses the preferred dimension of an embodiment and shall be interpreted as illustrative and not in a limiting sense. The device is to be commercially known as the trigger tome.

Spherical tipped guide probe 12, as shown in FIGS. 1-5, includes an about 2.5 cm long stainless steel spherical tipped probe that tapers from its proximal to distal end, with a proximal round diameter of about 2.5 mm and a distal rounded diameter of about 1.0 mm with an about 3.0 mm diameter spherical tip. Spherical tipped guide probe 12 is attached to the bottom part of sheath 16. Spherical tipped guide probe 12 is curved.

Dorsal outrigger spherical tipped guide 14, as shown in FIGS. 1-5, includes an about 5 mm long by about 1 mm diameter stainless steel spherical tip outrigger that extends from the distal top part of sheath 16 and has an about 2 mm diameter spherical tip at its terminal end. It may extend at about a 20 to 30 degree angle.

Figure 5:
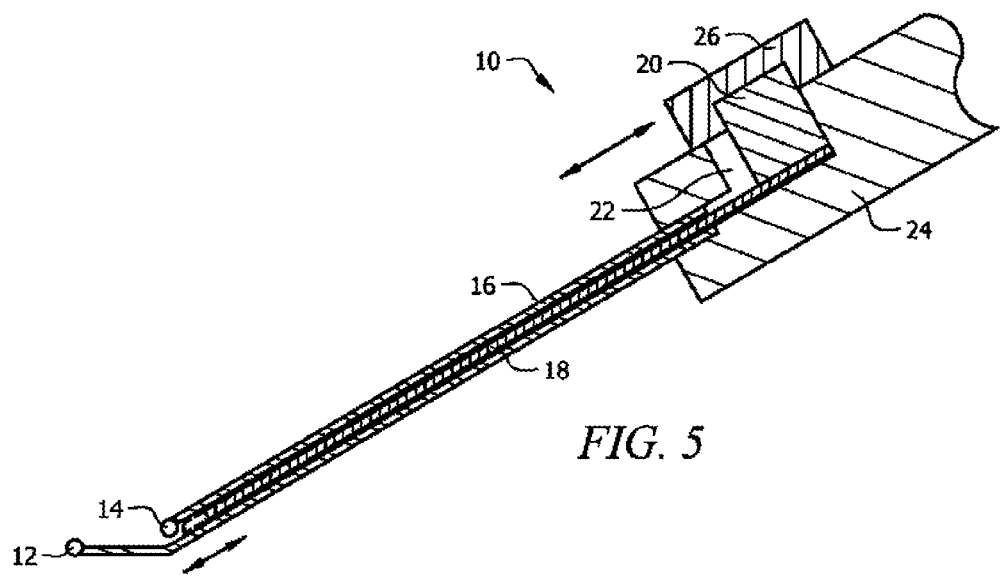
FIG. 5 is a cross sectional view of an embodiment of the device taken along line 5-5 in FIG. 2.
Figure 6:
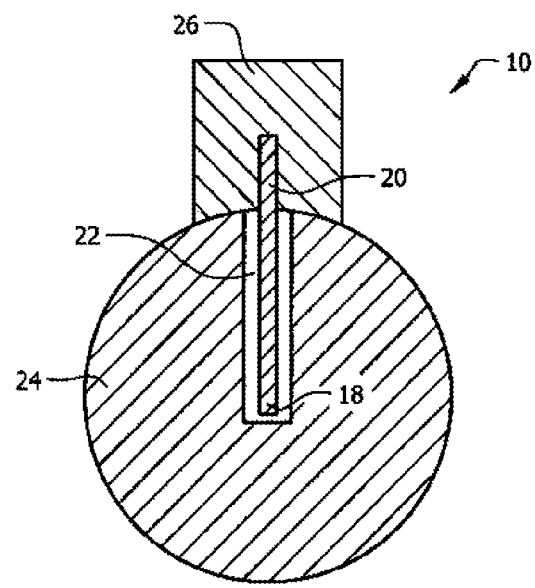
FIG. 6 is a cross sectional view of an embodiment of the device taken along line 6-6 in FIG. 4.

Sheath 16, as shown in FIGS. 1-3, includes a hollow tube about 6 cm long that has cross-sectional dimensions of about 2.5 mm by 1.0 mm. Sheath 16 contains retractable cutting shaft 18, as shown in FIGS. 4-6. Sheath 16 attaches distally to spherical tipped guide probe 12 and proximally to handle 24.

Retractable cutting shaft 18, as shown in FIGS. 4-6, includes an about 7.5 cm long piece of stainless steel having a cross-sectional dimension of about 0.7 mm by 2.2 mm, with a distal spade or square-shaped highly sharpened tip at the terminal end and connecting to sliding flag 20. When not deployed, the spade tip resides about 3 mm proximal to the terminal end of sheath 16.

Sliding flag 20, as shown in FIGS. 4-6, includes an about 1.0 mm by 10 mm by 1.5 mm stainless steel flag-like plate that attaches through a weld to retractable cutting shaft 18 inferiorly and is contained within handle 24 and translating about 5 mm proximal to distal within handle cavity 22. Sliding flag 20 attaches on its superior surface to blade deployment switch 26 by being firmly embedded in a slot in the base of the knob. Sliding flag 20 and switch 26 essentially form a trigger mechanism for deploying cutting shaft 18.

Handle 24, as shown in FIGS. 1-6, includes a knurled plastic or acrylic, round, tubular, solid structure measuring about 2.0 cm diameter and about 7.0 cm in length. Handle 24 contains handle cavity 22 that is oriented in the long axis of device 10, measuring about 1.5 cm by 1.3 mm by 1.0 cm deep. Handle cavity 22 originates on the surface and terminates at the equatorial center of device 10. Handle 24 also contains an about 2.5 mm by 1.0 mm slot that contains the proximal extension of retractable cutting shaft 18 that allows it to attach to sliding flag 20.

Handle cavity 22, as shown in FIGS. 4-6, is contained within handle 24 and contains sliding flag 20. Handle cavity 22 extends radially from the equatorial center of handle 24 about 1.0 cm to the surface.

Blade deployment switch 26, as shown in FIGS. 1-6, includes an about 2.0 cm by 0.8 cm by 0.8 cm plastic switch 26 attached firmly to sliding flag 20 and allows the thumb of the device operator to deploy the cutting blade once spherical tipped guide probe 12 is guided into position.

Spherical tipped guide probe 12 attaches to the distal bottom tip of sheath 16. Dorsal outrigger spherical tipped guide 14 is attached to the top of the distal part of sheath 16. Sheath 16 contains retractable cutting shaft 18 that cuts the pulley tissue when deployed. Sheath 16 is attached to handle 24, which in turn contains a tunnel (that is essentially an extension of sheath 16 within handle 24) and handle cavity 22 that contains and guides the proximal part of retractable cutting shaft 18 and attached sliding flag 20. Sliding flag 20 links retractable cutting shaft 18 to blade deployment switch 26.

The elements function together to act as a precise cutting guide for the A-1 pulley. Spherical tipped guide probe 12 goes through the small incision subcutaneously and is used to find the edge of the pulley. Once found, probe 12 is guided to the end of the pulley and its position is verified clinically and/or under radiographic or sonographic guidance. After proper position is assured, the cutting blade is deployed by pushing and holding blade deployment switch 26. This deploys the sharp end of retractable cutting shaft 18 3 mm beyond sheath 16. Device 10 is then pushed utilizing handle 24 along the pulley about 1 to 2 cm until the pulley is completely released or where resistance is no longer felt.

The patient's finger is anesthetized with lidocaine infiltration using a needle and syringe at the level of the distal palmar crease directly over the A1 pulley and palmar digital crease. A small puncture incision is then made over the palmar digital crease centrally using a #11 blade. Spherical tipped guide probe 12 is introduced centrally and subcutaneously over the tendon sheath and directed down at a 45 degree angle. Through probing with spherical tipped guide probe 12, the distal edge of the A1 pulley is located and spherical tipped guide probe 12 is passed below the pulley from distal to proximal in line with the flexor tendon until it is felt to push beyond the leading edge of the A1 pulley. The placement of spherical tipped guide probe 12 is verified clinically by wiggling it back and forth in the plane of the operating surface to make sure spherical tipped guide probe 12 is contained in the pulley. The placement of spherical tipped guide probe 12 and avoidance of the digital vessels is then confirmed under ultrasound guidance. Once correct placement is confirmed, the blade is deployed and device 10 pushed centrally and proximally along the A1 pulley completing the release.

Figure 7A:
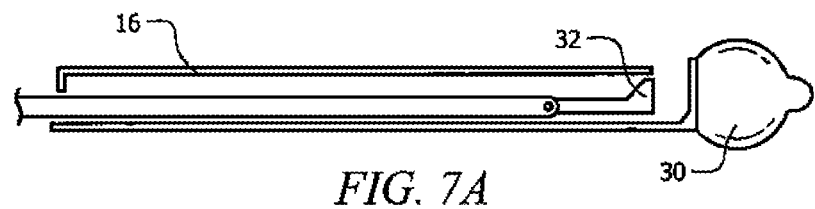
FIG. 7A is a side view of an embodiment of the device utilizing a crochet hook type blade as stowed.
Figure 7B:
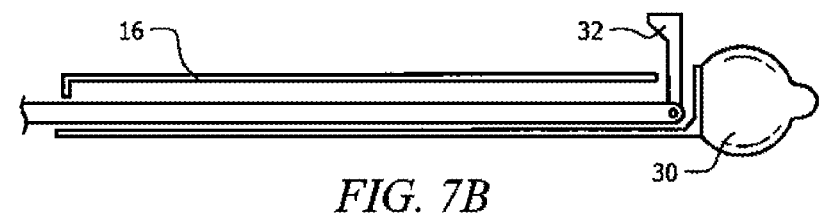
FIG. 7B is a side view of an embodiment of the device utilizing a crochet hook type blade as deployed.
Figure 8:
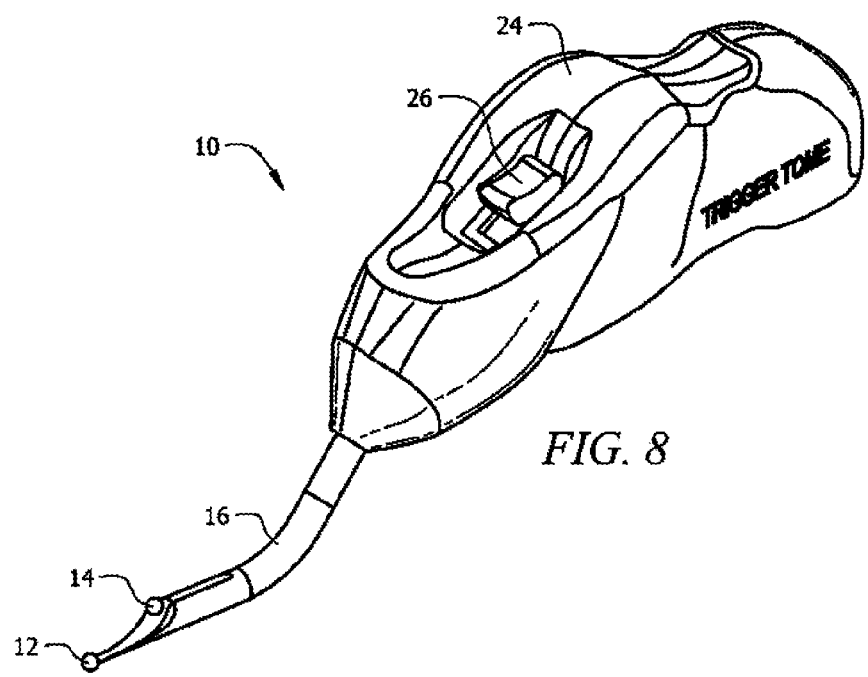
FIG. 8 is an upper perspective view of a commercial embodiment of the device utilizing a blade deployment mechanism.
Figure 9:
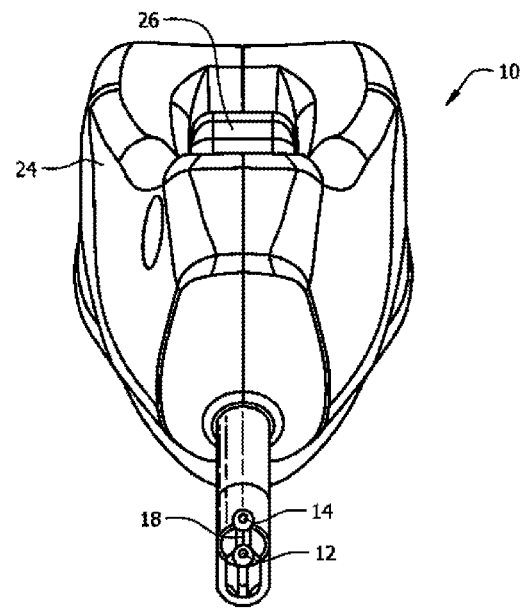
FIG. 9 is a front view of a commercial embodiment of the device utilizing a blade deployment mechanism.
Figure 10:
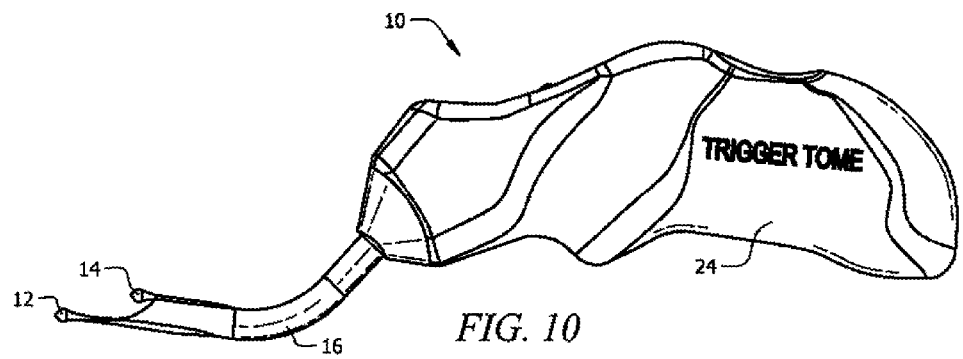
FIG. 10 is a side view of a commercial embodiment of the device utilizing a blade deployment mechanism.
Figures 11, 12:
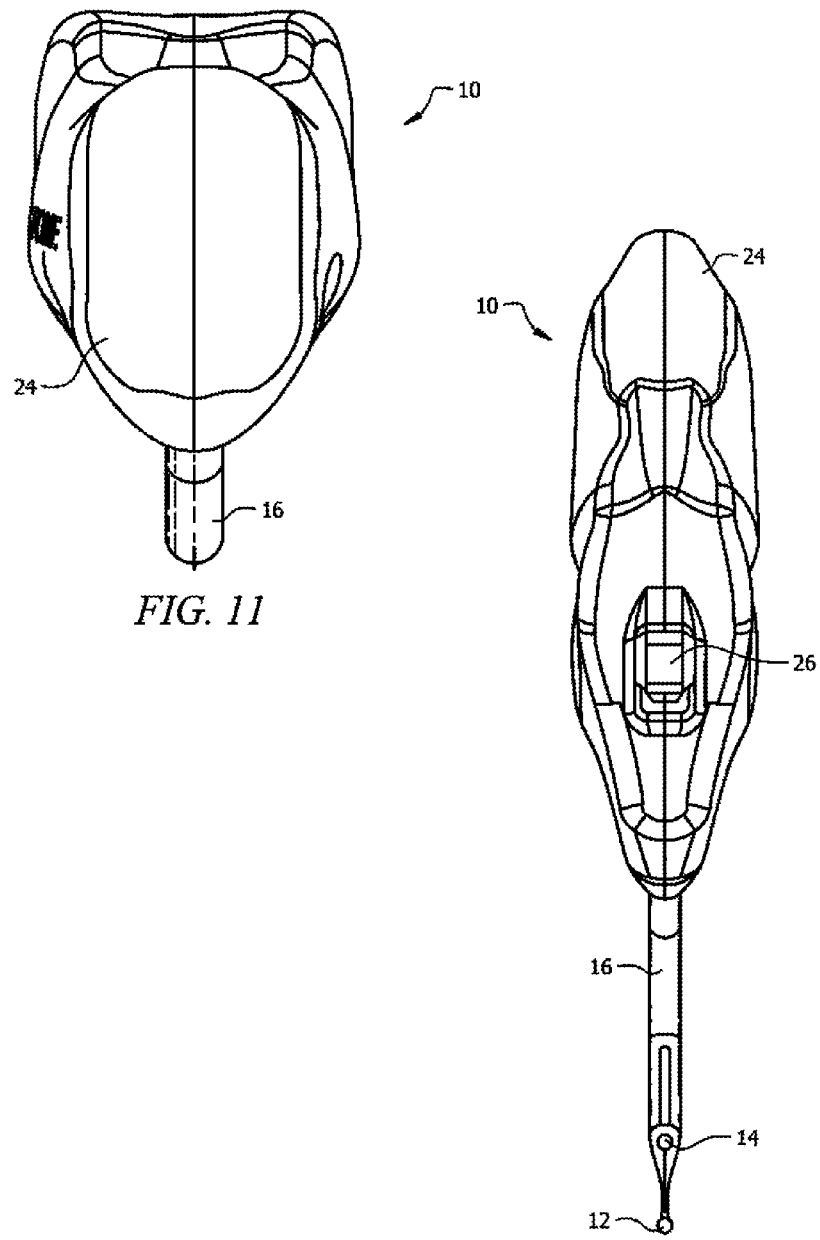
FIG. 11 is a rear view of a commercial embodiment of the device utilizing a blade deployment mechanism.
FIG. 12 is a top view of a commercial embodiment of the device utilizing a blade deployment mechanism.
Figure 13:
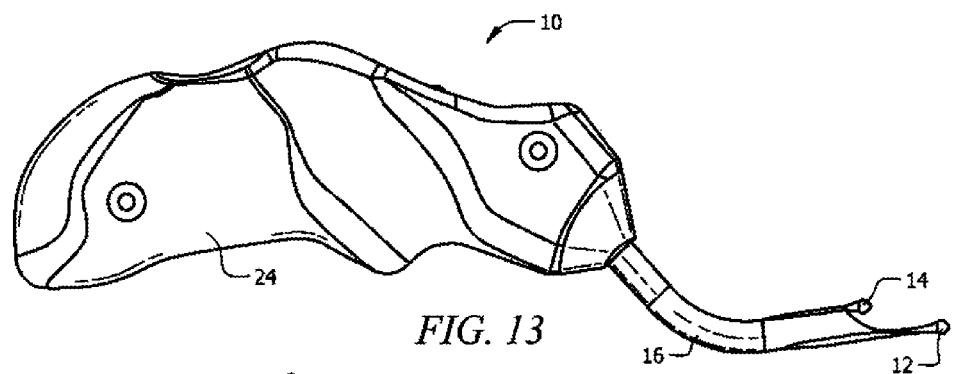
FIG. 13 is a side view of a commercial embodiment of the device utilizing a blade deployment mechanism.
Figure 14:
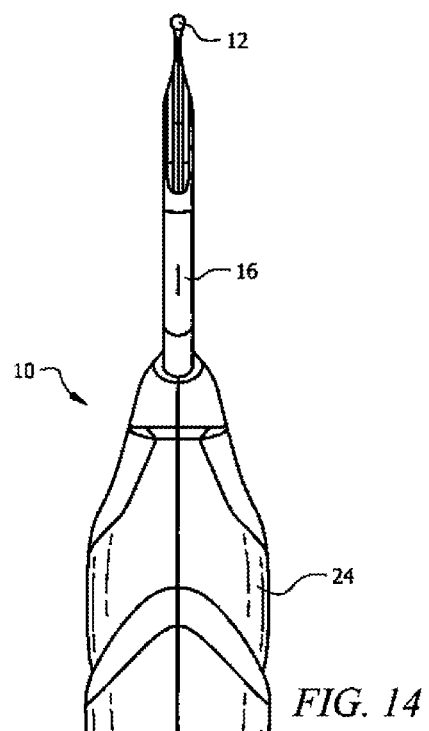
FIG. 14 is a bottom view of a commercial embodiment of the device utilizing a blade deployment mechanism.

In an alternative embodiment, as shown in FIGS. 7A and 7B, the device is made with sheath 16 extending to the level of spherical tipped guide probe 30 and deploys a crochet hook type blade 32 after being passed completely past the A1 pulley through the pulley tunnel. The crochet hooked blade 32 is then deployed and pulled backward to release the pulley from distal to proximal instead of proximal to distal. A trigger mechanism deploys crochet hook type blade 32.

FIGS. 8-14 illustrate a commercial embodiment of the claimed invention.

Figure 15:
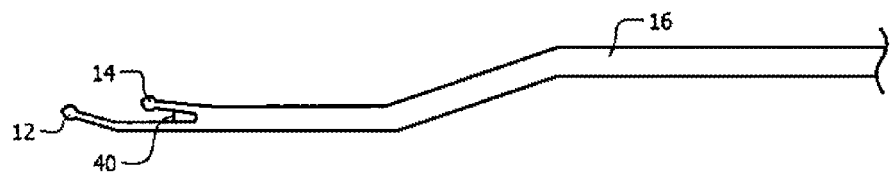
FIG. 15 is a side view of an embodiment of the device having a static blade.
Figure 20:
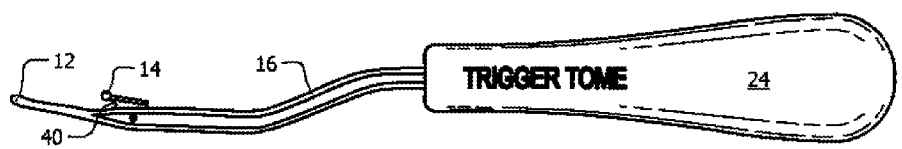
FIG. 20 is a side view of a commercial embodiment of the device having a static blade.
Figure 21:
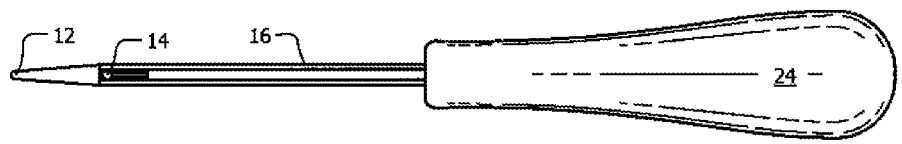
FIG. 21 is a top view of a commercial embodiment of the device having a static blade.

In an alternate embodiment, as shown in FIGS. 15, 20, and 21, an affixed cutting blade 40 is located at the distal end of sheath 16 between dorsal outrigger spherical tipped guide 14 and spherical tipped guide probe 12. In this embodiment, the trigger mechanism is unnecessary. Specifically, FIG. 15 depicts a static blade 40 at the apex of the two spherical tipped guides. The longer spherical tipped guide is turned up to facilitate placement under the pulley and the whole device is pushed forward to release the pulley.

Figure 16:
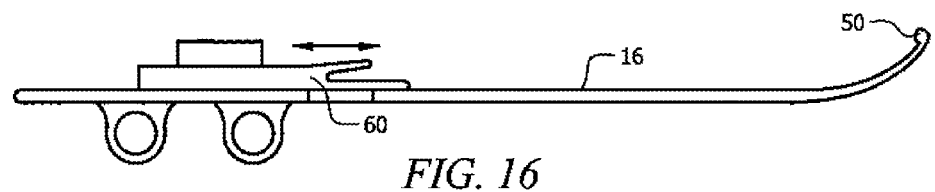
FIG. 16 is a side view of an embodiment of the device having a sliding blade.

FIG. 16 depicts an embodiment where shaft 16 is turned up at tip 50. Tip 50 is placed under the pulley and the curved tip locates the end of the pulley tunnel by feel. Sliding blade 60 slides along shaft 16 dividing the pulley by pushing slide blade 60 rather than the whole instrument.

Figure 17:
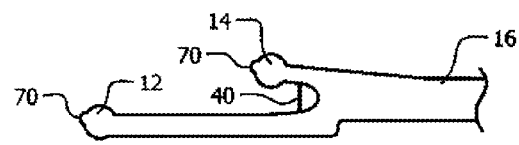
FIG. 17 is a side view of an embodiment of the device having a static blade.

FIG. 17 depicts an embodiment of the static or deployable blade 18 which has spherical tips 12 and 14 with small protrusions 70 (or nipples) at the tips to facilitate placement under the pulley and travel through the subcutaneous soft tissues above the pulley.

Figure 18:
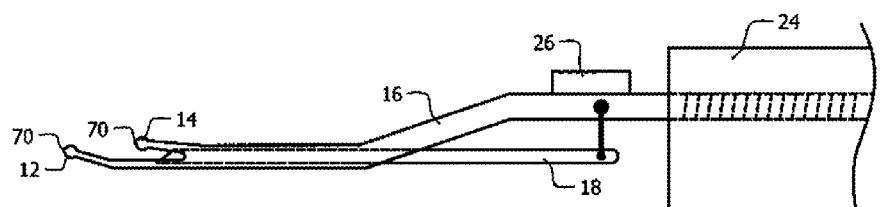
FIG. 18 is a side view of an embodiment utilizing a alternate blade deployment mechanism.
Figure 19:
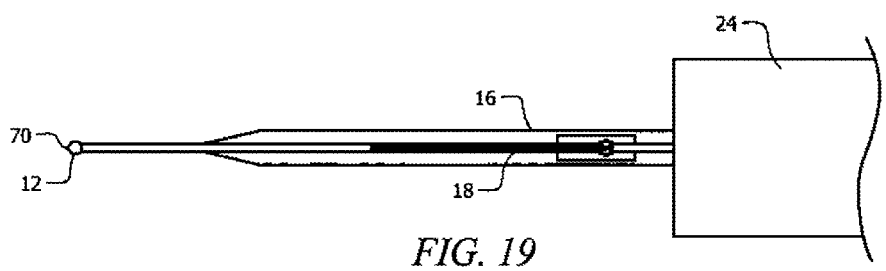
FIG. 19 is a bottom view of an embodiment utilizing a alternate blade deployment mechanism.

FIGS. 18 and 19 depict an alternate deployment mechanism for extending and retracting blade 18. Specifically, deployment switch 26 and cutting shaft 18 are in mechanical communication via a lever.

Figure 22:
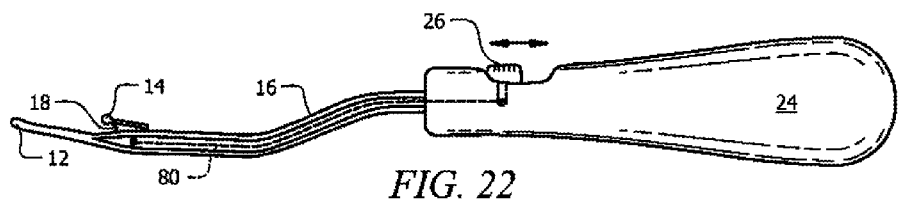
FIG. 22 is a side view of a commercial embodiment of the device utilizing a blade deployment mechanism.
Figure 23:
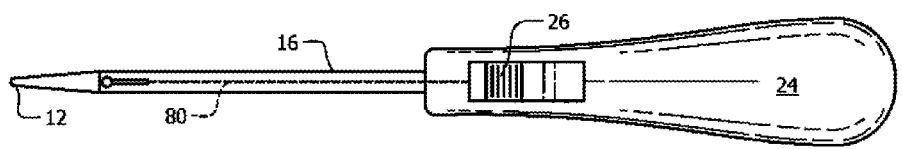
FIG. 23 is a top view of a commercial embodiment of the device utilizing a blade deployment mechanism.

Similarly, FIGS. 22 and 23 depict an alternate deployment mechanism for extending and retracting blade 18. In FIGS. 22 and 23, wire 80 extends through hollow shaft 16 attached to blade 18 allowing it to be retracted to the level of ball 14 so the instrument can be placed safely in the blunt mode and blade 18 deployed and instrument pushed forward to divide the pulley.

Figure 24:
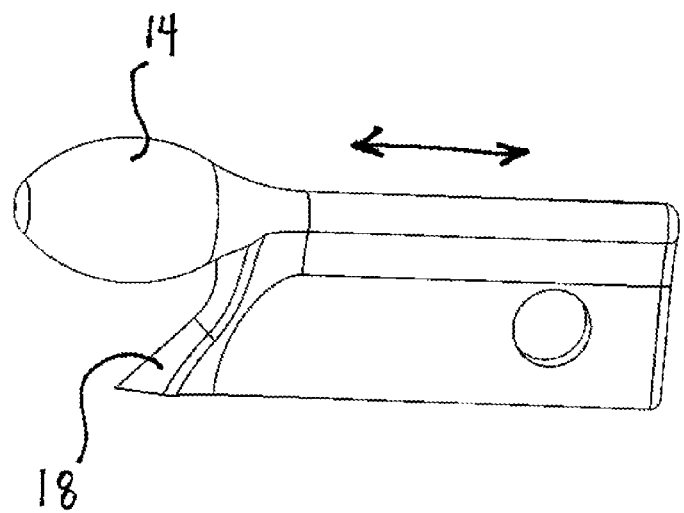
FIG. 24 is a side view of an embodiment of the device having the dorsal outrigger spherical tipped guide and retractable cutting shaft 18 as one component.

In an alternate embodiment, as shown in FIG. 24, dorsal outrigger spherical tipped guide 14 is disposed at the top, distal end of retractable cutting shaft 18. Because dorsal outrigger spherical tipped guide 14 is disposed at the top, distal end of retractable cutting shaft 18, they both extend and retract together as retractable cutting shaft 18 is deployed. Instead of two separate components, the two are essentially formed as one component.

In other embodiments, device 10 is used to release other tendon sheaths and slips of tissue in the body by providing safe subcutaneous guidance and subsequent effective cutting. Device 10 can be used unmodified for DeQuervain's release, posterior tibial tendon release, tarsal tunnel release, and, through a variation of spherical tipped guide probe 12 concept and device size, be used to perform a carpal tunnel release with ultrasound guidance through a small puncture incision and a plantar fascial release. Variations can also be used to perform fasciotomy incisions in the leg and forearm for compartment syndromes.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

What is claimed is:

1. A device for minimally invasive tendon sheath release, comprising:
   a handle having a cavity contained therein;
   a sheath having a proximal and a distal end wherein the proximal end projects from the cavity and the distal end has a top and a bottom portion;
   a spherical-tipped guide probe attached to the bottom portion of the distal end of the sheath;
   a spherical-tipped dorsal outrigger guide attached at the top portion of the distal end of the sheath; and
   a cutting blade disposed between the guide probe and the dorsal outrigger guide.

2. The device of claim 1, wherein the dorsal outrigger guide is disposed at an angle relative to the sheath.

3. The device of claim 1, wherein the guide probe is tapered.

4. The device of claim 1, wherein the guide probe is curved.

5. The device of claim 1, wherein the sheath is curved.

6. The device of claim 1, wherein the guide probe is adapted to extend at least a length of an A-1 pulley of a patient.

7. The device of claim 1, wherein the cutting blade is disposed at an angle.

8. The device of claim 1, wherein the cutting blade is static.

* * * * *